United States Patent

Harris

(10) Patent No.: US 6,719,807 B2
(45) Date of Patent: Apr. 13, 2004

(54) PROSTHETIC FOOT

(75) Inventor: Graham Harris, Basingstoke (GB)

(73) Assignee: Chas. A. Blatchford & Sons Ltd. (GB)

( * ) Notice: Subject to any disclaimer, the term of this patent is extended or adjusted under 35 U.S.C. 154(b) by 0 days.

(21) Appl. No.: 09/839,161

(22) Filed: Apr. 20, 2001

(65) Prior Publication Data

US 2002/0013628 A1 Jan. 31, 2002

(30) Foreign Application Priority Data

Apr. 26, 2000 (GB) .............................................. 0010184

(51) Int. Cl.[7] .................................................. A61F 2/66
(52) U.S. Cl. .............................. 623/55; 623/52; 623/53
(58) Field of Search ................... 623/47–56; A61F 2/66

(56) References Cited

U.S. PATENT DOCUMENTS

| | | | |
|---|---|---|---|
| 4,547,913 A | 10/1985 | Phillips | 623/27 |
| 4,653,455 A | 3/1987 | Eblen et al. | 123/506 |
| 4,653,723 A | 3/1987 | Rizk et al. | 251/282 |
| 4,791,958 A | 12/1988 | Brundage | 137/528 |
| 4,944,328 A | 7/1990 | Brundage | 137/528 |
| 5,037,444 A | 8/1991 | Phillips | 623/55 |
| 5,112,356 A * | 5/1992 | Harris et al. | 623/49 |
| 5,253,676 A | 10/1993 | Craig | 137/625.61 |
| 5,258,039 A | 11/1993 | Goh et al. | 623/55 |
| 5,376,169 A | 12/1994 | Hotomi et al. | 623/51 |
| 5,507,838 A | 4/1996 | Chen | |
| 5,509,937 A * | 4/1996 | Allard et al. | 623/55 |
| 5,549,711 A | 8/1996 | Bryant | |
| 5,551,466 A | 9/1996 | De Pieri | 137/1 |
| 5,597,014 A | 1/1997 | Vick | 137/625.23 |
| 5,639,066 A | 6/1997 | Lambert et al. | 251/282 |
| 5,653,767 A | 8/1997 | Allen et al. | 623/52 |
| 5,653,768 A * | 8/1997 | Kania | 623/55 |
| 5,876,184 A | 3/1999 | Marcott | 417/213 |
| 5,897,594 A * | 4/1999 | Martin et al. | 623/53 |
| 5,911,245 A | 6/1999 | Weber | 137/625.65 |
| 5,944,760 A | 8/1999 | Christensen | |
| 6,007,582 A * | 12/1999 | May | 623/55 |
| 6,089,470 A | 7/2000 | Teerman et al. | 239/88 |
| 6,129,766 A | 10/2000 | Johnson et al. | 623/49 |
| 6,206,934 B1 * | 3/2001 | Phillips | 623/53 |
| 2002/0116072 A1 * | 8/2002 | Rubie et al. | 623/55 |

FOREIGN PATENT DOCUMENTS

| | | | |
|---|---|---|---|
| GB | 2272747 | 5/1994 | |
| WO | WO 93/04645 | 3/1993 | |
| WO | WO94/10942 A1 | 5/1994 | |
| WO | WO96/04869 A1 | 2/1996 | |
| WO | WO 98/01092 A1 * | 1/1998 | A61F/2/66 |
| WO | WO 01/47444 A1 * | 7/2001 | A61F/2/66 |

OTHER PUBLICATIONS

Aug. 3, 2001. European Search Report for EP 01303759.3.

* cited by examiner

*Primary Examiner*—David H. Willse
*Assistant Examiner*—Javier G. Blanco
(74) *Attorney, Agent, or Firm*—Hale and Dorr LLP

(57) ABSTRACT

A prosthetic foot comprises an elongated, substantially two-dimensional, resilient toe member, an elongated, substantially two-dimensional heel member, and a substantially rigid carrier member. One end of each of the toe and heel members is independently connected to the carrier member. The toe and heel spring members can be selected independently so as to provide the wearer with personalized characteristics and responses at heel-strike, foot-flat, and toe-off.

16 Claims, 5 Drawing Sheets

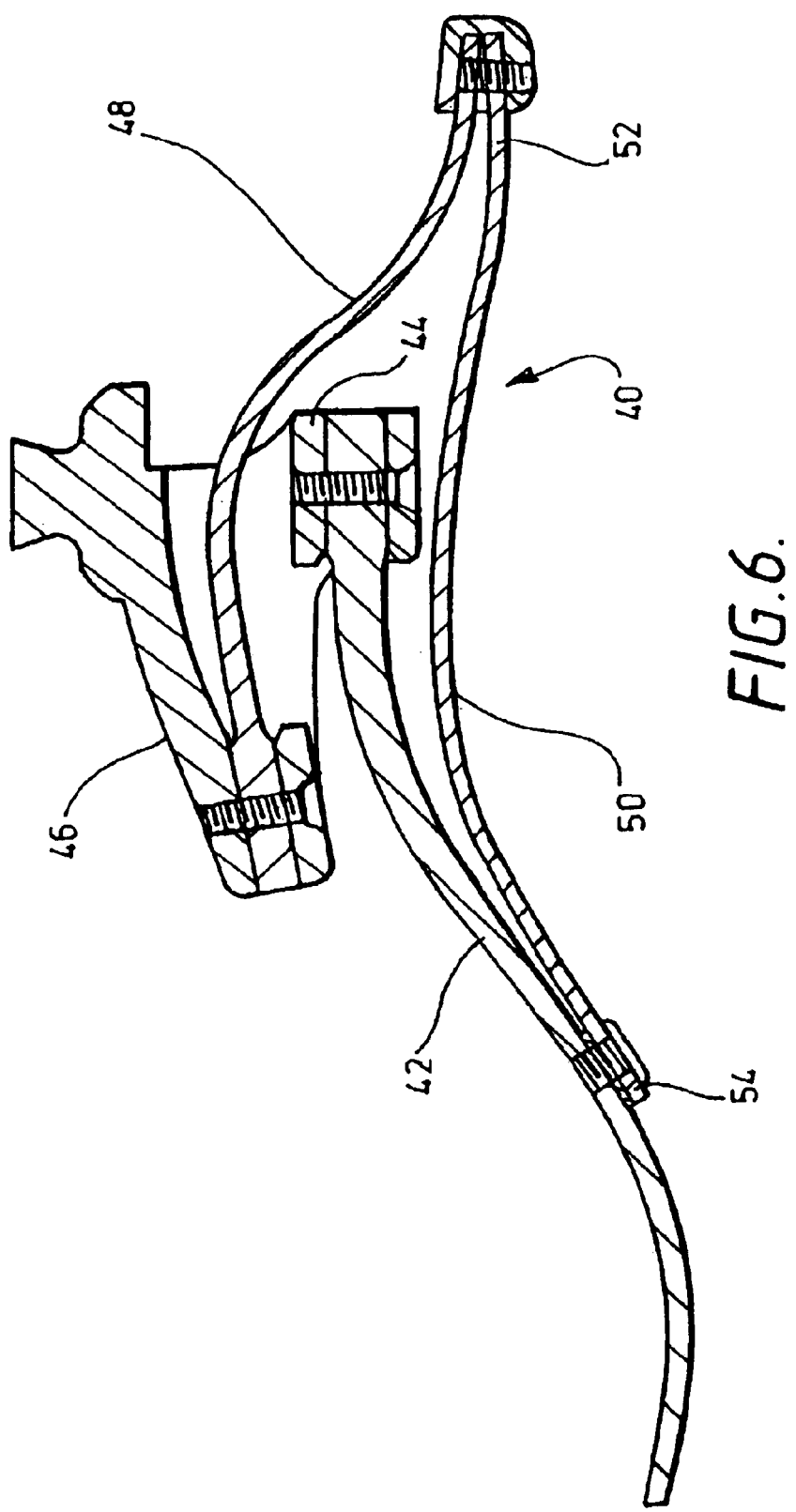

PROSTHETIC FOOT

RELATED APPLICATION

This Application claims priority to UK Application No. 0010184.0, Filed Apr. 26, 2000.

BACKGROUND OF THE INVENTION

1. Field of the Invention

This invention relates to a prosthetic foot.

2. Background Art

A very large number and variety of constructions of prosthetic feet are known. It is desirable to have a prosthetic foot that is reliable, lightweight, and that provides the flexibility and response matching as closely as possible to that of the natural foot it is to replace. It will be appreciated that different stresses and requirements arise depending on the age, weight, amputation level and general agility of the amputee.

U.S. Pat. No. 5,037,444 discloses a prosthetic foot that has a forefoot portion with a heel portion demountably and interchangeably connected thereto. The forefoot and heel portions are fabricated from polymer impregnated and encapsulated laminates, such as carbon fibres and/or fibreglass or synthetic fibres such as Kevlar. The demountable connection of the heel portion permits interchangeability of heel and forefoot portions to match the weight, stride and activity schedule of the wearer of the foot. The foot and heel portions contain spring sections, and are rigidly secured together.

U.S. Pat. No. 4,547,913 discloses another simple construction of composite prosthetic foot and leg having leg, foot and heel portions of substantial elastic flexibility. The three portions are rigidly joined together within an encircling binding.

WO-A-96/04869 discloses a more complicated foot prosthesis having a cushioned ankle, in which an ankle block, formed of a resilient material or a bladder having desired compliance and energy return characteristics, is sandwiched between a lower foot plate element that extends from toe to heel and an upper ankle plate element. Spring elements may be embedded in the ankle block or bladder to increase the rigidity of the prosthetic foot and to improve the degree of energy storage and return.

SUMMARY OF THE INVENTION

It is one object of the present invention to provide a prosthetic foot that is lightweight, of relatively simple construction, and which offers a natural feel that can be adjusted to the requirements of the wearer.

In accordance with a first aspect of the present invention, there is provided a prosthetic foot comprising:

- a substantially two-dimensional, preferably elongate, resilient toe member;
- a substantially two-dimensional, preferably elongate, resilient heel member; and
- a substantially rigid carrier member; wherein one end of each of the toe and heel members is connected to the carrier independently of the other of said members.

The foot of the invention can thus provide two spring elements, for the toe and for the heel, which are independently secured to a rigid component. By this means each element can be individually selected to provide the wearer with the required characteristics and responses at heel-strike, foot-flat, and toe-off independently of the other element. Thus, a pair of elements can be matched to each other to suit a specific individual. Furthermore, the resilience of one or both of the elements of a foot may be adjustable, either by the wearer on demand, for example to accommodate different levels of activity of the user, or by being pre-set during initial fitment of the prosthesis to the wearer.

It is important to match the heel and toe members in order to achieve a smooth transition from heel strike to toe off with maximum energy storage and return. If the foot is not balanced, the gait can become jerky and less energy efficient. Some of the effects of poorly matched functional areas in a foot are listed below:

1. Heel too soft: Sinking at heel strike. Toe appears hard (see below).
2. Heel too hard: Jarring at heel strike. Rapid progression to toe off.
3. Toe too soft: Spring does not return sufficient energy. Rapid progression through roll over to toe off.
4. Toe too hard: Difficult to progress to toe off. Back pressure on stump.
5. Heel and toe too hard: Little energy absorbed or returned. Jerky, jarring action.
6. Heel and toe to soft: Foot does not return energy. Amputee spends extended time on foot during support phase.

Since in the foot of the invention, the resilient members will be supplied as a matched pair, the alignment shift feature will them be used to fine tune the foot rapidly to the amputee's requirements.

Preferably, the toe member of the foot extends forwardly of the foot from its connection with the carrier member and the heel member extends rearwardly of the foot from its connection with the carrier member, and the toe and heel members overlap one another in the region between the connections. The overlapping relationship of the toe and heel members allows each one, acting as a spring element, to be individually designed to the required specification, including specifically allowing for its length to be optimised, whilst maintaining the overall length of the completed prosthesis within the natural shoe size of the wearer. Preferably the toe member extends over the heel member. The arrangement in which the toe member lies above the heel member allows the use of bigger springs, whilst minimising the overall height of the foot. This has the advantage that the foot of the invention can be fitted even to amputees having relatively long residual stumps. Furthermore, the longer the resilient members can be, the straighter they can be made for any given required wearer characteristics. A straighter member not only is easier to manufacture, but problems of high stress resulting from significant curvature are also minimised. Since a resilient foot member may be of laminate construction, and act structurally as a beam, it could become loaded in a direction which tends to open the radius, resulting in failure by delamination. This is overcome, or at least alleviated, either by enclosing the member within an encapsulating layer (which can be comparatively expensive) or by thickening the member locally (which can reduce the flexibility of the beam). Such problems can thus be avoided, or at least minimised, by the straighter members that are allowed by the foot construction of the present invention.

It is to be appreciated, however, that with suitable materials, it may be possible to design the prosthetic foot with toe and heel members that do not need to overlap. In such a foot, the rigid carrier member will be located longitudinally intermediate the toe and heel members.

The carrier member may define an enclosure, preferably a rectilinear cage, wherein one end of one of the toe and heel members extends into the enclosure and is secured therewithin, and the other of the toe and heel members is secured to the outside of the enclosure. The preferably cage-like structure of the carrier member can thus provide the required rigidity for the independent mounting of the two resilient foot members, whilst keeping the weight to a minimum. The rigid carrier also serves as the attachment point of the foot to the limb, thus avoiding the need for any stiffening that would otherwise be necessary, and disadvantageous, if the ankle of the limb were to be connected directly to one of the resilient foot members.

In accordance with a second aspect of the present invention, there is provided a prosthetic foot comprising a resilient, and preferably elongate, toe and/or heel member, in which the or each member is of generally two-dimensional configuration but is of channel-section, for example U-, V-, or C-shaped section.

Such a configuration of member can thus not only allow deflection in the Medial-Lateral (M-L) direction whilst maintaining relatively rigidity in the Anterior-Posterior (A-P) direction, but can do this using a relatively thin-walled, and thus, lightweight, component. In general, a thin-walled channel section beam has the following advantages over a rectangular section beam:

(a) it can carry bending loads more efficiently, and consequently it uses less material and is therefore lighter, and potentially cheaper;

(b) it has comparatively low torsional stiffness, which allows the toe member of a prosthetic foot, for example, to twist and to conform to uneven surfaces. Conventional prosthetic foot configurations achieve M-L compliance through the use of either a split toe member, which is potentially noisy and structurally weaker than a non-split configuration, or a separate resilient ankle, which adds weight and is also to some extent, and disadvantageously, energy absorbing; and (c) it is better suited to the strength characteristics of a composite material. Because of the fibre buckling failure mode of a composite material under compressive load, typical materials are generally stronger in tension than in compression. In a rectangular beam section under bending, this comparatively low compressive strength becomes the limiting stress for the beam. A channel beam section, however, has an offset neutral axis in bending and this allows the high tensile strength to be better exploited and thus the efficiency of the overall beam design to be improved.

It will be appreciated that a toe and/or heel member of the said first aspect of the prosthetic foot of the invention may be formed in accordance with the said second aspect of the invention.

The toe and heel members may be releasably mounted to the carrier member, for example using bolts and nuts, or alternating they may be permanently secured thereto following final fitting trials with the amputee. Thus, foot members having different characteristics, for example spring rate, may be provided for different activities of the wearer, for example, normal walking or a sporting activity. It is also envisaged that a foot having given toe and heel members may be adjustable for different activities. For example, an adjustable stop may be provided, preferably mounted on the carrier member, to limit the flexing of the toe and/or heel member with respect to the carrier member.

The toe and heel members may be made from any suitable material, but preferably from high-strength, lightweight, resin-impregnated fibrous material. Carbon fibre, glass fibre, or Kelvar composites, for example, are particularly suitable materials. The carrier member is also preferably formed from a lightweight, high strength material, and may be formed as a moulded composite material. It is also envisaged that the carrier member may be made from a low density metal, such as aluminum or titanium, or it may be made from stainless steel. The toe member may be slit longitudinally along at least part of its length, to facilitate lateral movement of the foot in use.

The toe, heel and carrier members will usually be enclosed within a cosmesis, with the ends of the toe and heel members that are remote from their attachment to the carrier member being secured thereto, preferably being retained within reinforced slots of the cosmesis.

Since the foot of the invention may be assembled from the three components discretely, it is possible to make the final assembly within the shell (cosmesis) itself. This allows a relatively high level of interlock, without the stretching of the foot shell that can occur with conventional configurations. A secure fitment of the toe and heel members within the foot shell is required in order to avoid the generation of noise in use.

In a third aspect of the present invention, there is provided a prosthetic foot in accordance with one or both of said first and second aspects of the invention, wherein a further resilient foot member is secured to the said toe and heel members at locations spaced apart from their securement to the carrier member.

Preferably, the further foot member, which preferably is substantially two-dimensional, is secured at one of its ends to the heel member at its end remote from the carrier member. The further foot member may be secured at its other end to the toe member at a region thereof intermediate its attachment to the carrier member and its free end.

The toe, heel and further foot members are preferably of generally elongate S-shape.

In accordance with a fourth aspect of the present invention, there is provided a method of forming a prosthetic foot, wherein the foot comprises a resilient toe member, a resilient heel member, a substantially rigid carrier member, and a cosmesis, in which the three said members are secured together and to the cosmesis subsequent to the introduction of the three members into the cosmesis.

BRIEF DESCRIPTION OF THE DRAWINGS

Embodiments of a prosthetic foot, each in accordance with the present invention, will now be described, by way of example, with reference to the accompanying drawings, in which:

FIG. 4 is a section through a modified member of the foot of the first embodiment;

FIG. 6 is sectional elevation of the foot of FIG. 5.

DETAILED DESCRIPTION OF THE PREFERRED EMBODIMENT

Figure 1:
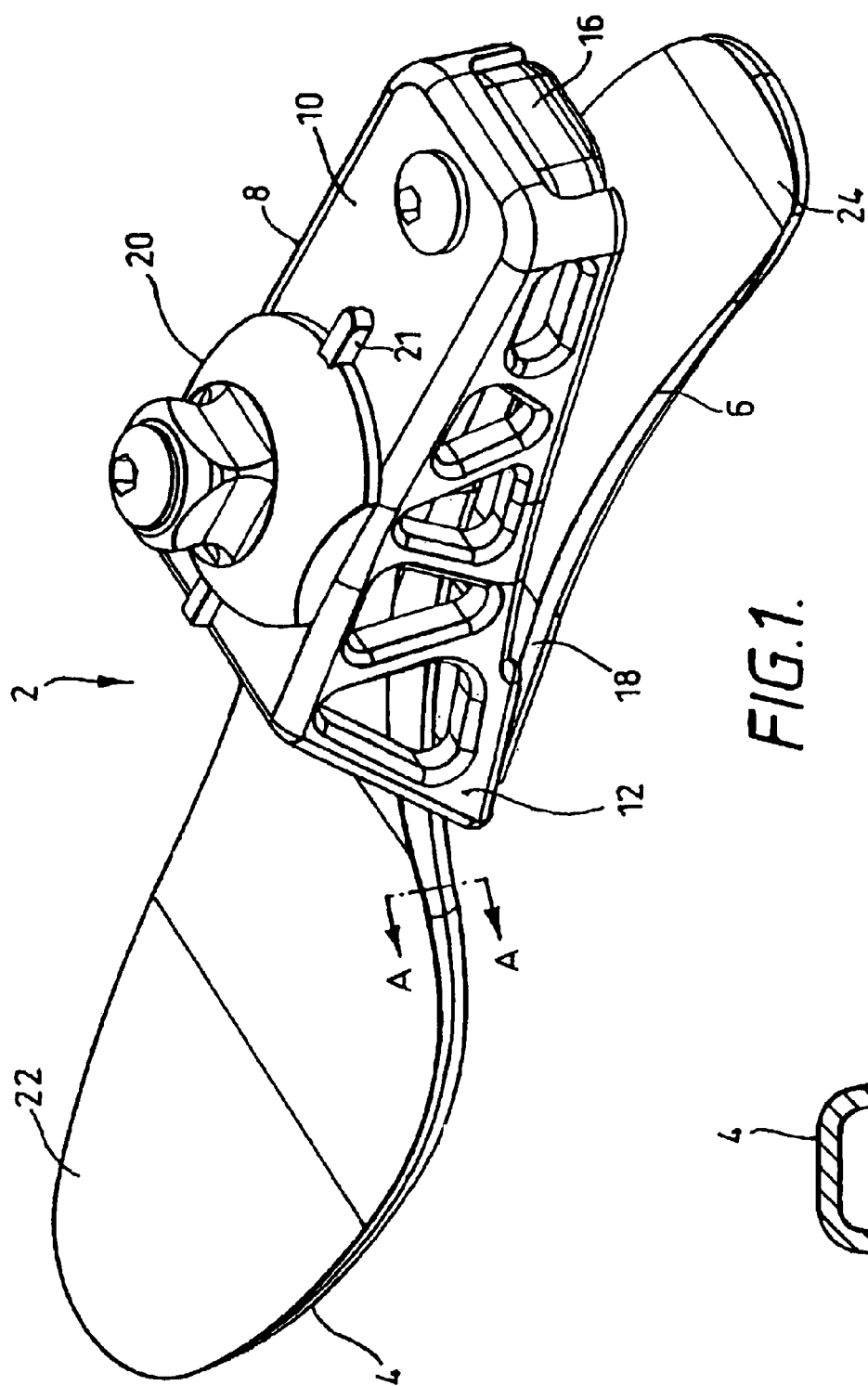
FIG. 1 is an isometric view of a first embodiment of a foot.
Figure 2:
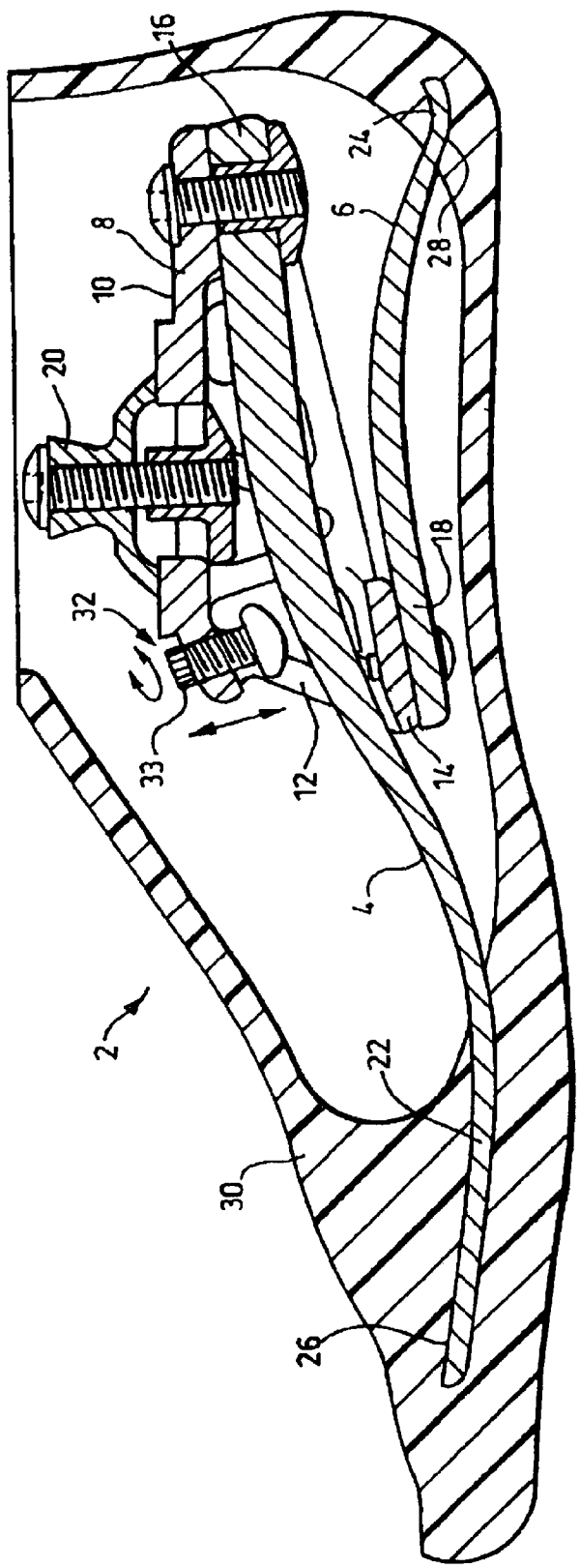
FIG. 2 side elevation of the foot of FIG. 1 encased within a cosmesis.
Figure 3:
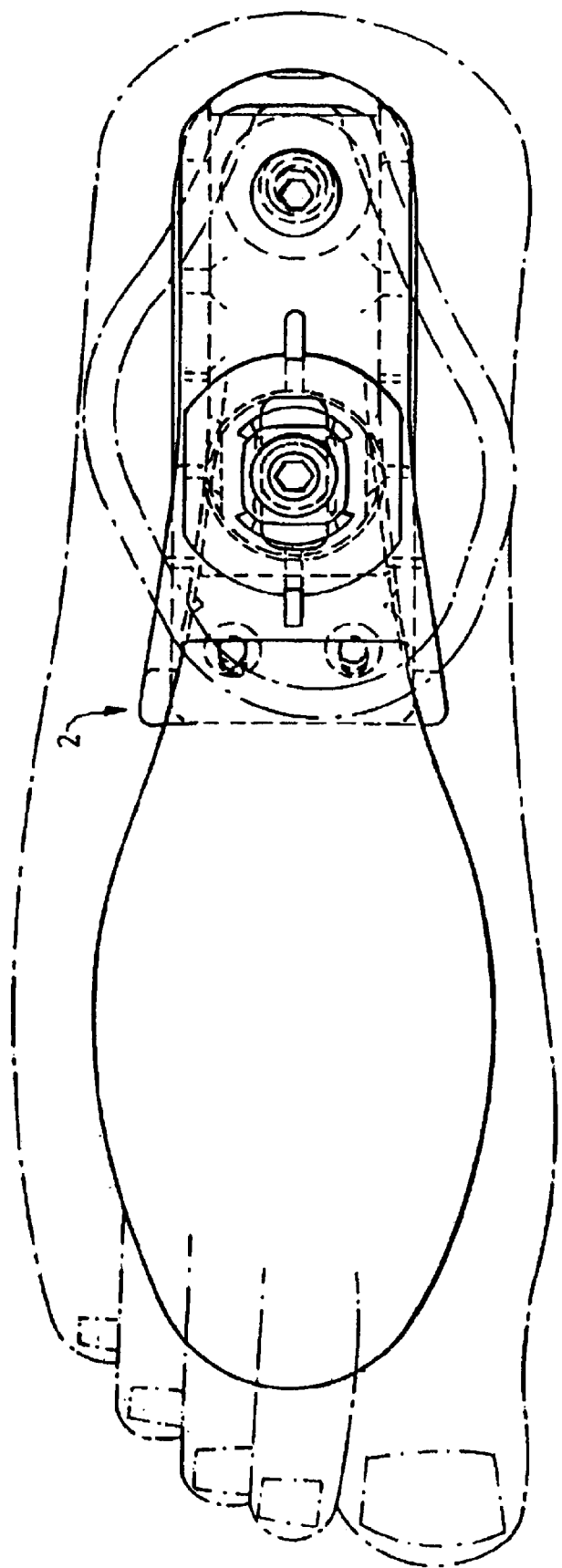
FIG. 3 is a plan view of the foot of FIG. 1 superimposed upon a natural foot.

Referring to FIGS. 1 to 3, a prosthetic foot 2 comprises a toe spring 4 and a heel spring 6. The springs 4 and 6 are made of carbon fibre composite material and are of generally two-dimensional configuration. The toe spring 4 is of an elongate S-shape, and the heel spring is flatter. The foot 2 also comprises a rigid stainless steel carrier 8 having a generally-planar upper plate 10, a pair of apertured side walls 12 and a lower cross member 14 at the forward end thereof. The panels 10, 12 and 14 define a generally-open cage-like structure of the carrier 8. The rearward end 16 of the elongate toe spring 4 is bolted to the plate 10 at the rear of the carrier 8. The forward end 18 of the heel spring 6 is bolted to the cross member 14 of the carrier 8. Away from these bolt attachment regions, the springs 4 and 6 are not in contact with the carrier 8 in normal usage, and are independently mounted thereon. An ankle attachment base 20 is slidably mounted on a track 21 on the upper plate 10 of the carrier 8, for receiving an ankle and/or leg member as necessary.

The forward end 22 of the toe spring 4, and the rearward end 24 of the heel spring 6 engage within respective slots 26 and 28 in a cosmesis 30 of the foot 2. Also shown is a stop 32 that extends downwardly into the cage of the carrier 8 from the upper plate 10 thereby to limit movement of the spring 4. The stop 32 is adjustable by means of a knurled knob 33 and is shown in the mid position. In practice, the stop 32 would be either fully raised or fully lowered in order to avoid bottoming of the toe spring 4 during normal walking, which would give rise to an undesirable two stage action.

It is to be appreciated that since each of the springs 4 and 6 is attached independently of the other to the rigid carrier 8 and is allowed to move generally freely therewithin, the characteristics of these two components can be adjusted independently of each other to suit the requirements of the wearer. In particular, the desired heel strike characteristics can be achieved by suitable selection of the heel spring 6, and the desired toe off characteristics to suit the wearer can be achieved by suitable selection of the toe spring 4. The combination of particular toe spring 4 and heel spring 6 can also be selected to give the desired flat foot characteristics of the foot 2 appropriate to the specific wearer. As can be seen, the toe spring 4 and heel spring 6 overlap one another within the designed and required overall length of the foot. In this way, relatively longer springs can be incorporated for added versatility in selecting the required characteristics of the foot overall, without requiring the complete foot to be unduly long.

The stop 32 may either be pre-set or can be adjustable by the wearer, and it is envisaged that this may be utilised for more active uses of the wearer, such as partaking in sports, in which restricted movement of the toe spring 4 may be desirable.

The ankle attachment base 20 may be selectively positioned longitudinally along the track 21 to suit the wearer.

FIG. 4 shows a section along the line A—A of FIG. 1 through the toe spring 4. Thus, the spring 4 is of channel section, which allows the use of a thin-walled open-section spring to give M-L deflection. It is to be appreciated that although the foot to FIGS. 1 to 3 has been shown in the preferred form of having the toe spring 4 lying above the heel spring 6 with the springs attached to opposite ends of the carrier 8, it is envisaged that the heel spring may be configured to lie above the toe spring, with the front end of the heel spring attached to the front end of the upper panel of the carrier and the rear end of the toe spring attached to a cross member at the rear of the carrier.

It is also be understood, however, that where the relatively long lengths of springs that can be accommodated within these arrangements is not required in order to achieve the desired characteristics of the foot for a particular wearer, then the springs need not overlap one another, and the rear of the toe spring can be secured to the front end of the carrier, and the front end of the heel spring can be secured to the rear end of the carrier.

Figure 5:
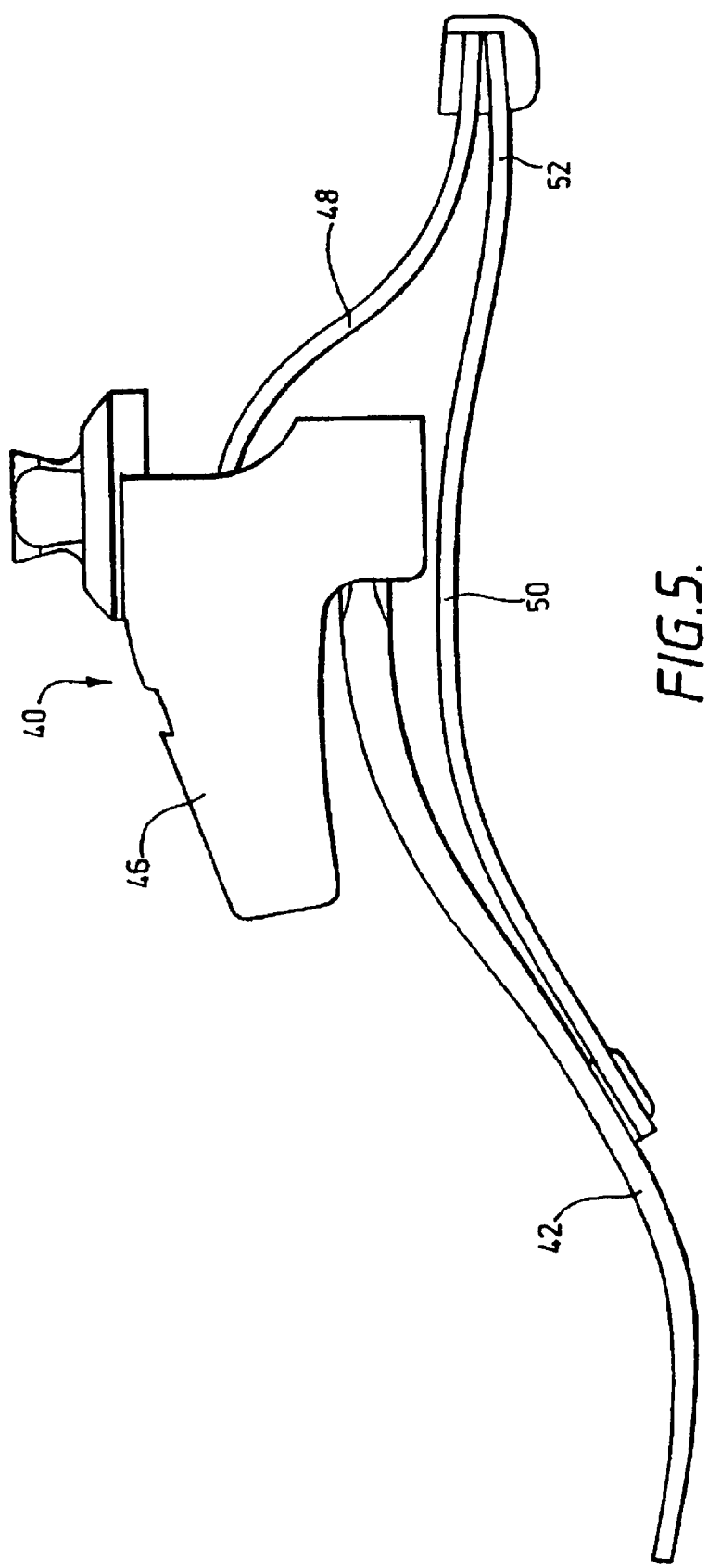
FIG. 5 is a side elevation of a second embodiment of the foot.

Referring to the alternative embodiment of prosthetic foot 40 shown in FIGS. 5 & 6, a toe spring 42 is bolted to a transverse member 44 at the rear of a stainless steel carrier 46. The foot 40 of this embodiment has a further spring, a wave spring 50, the rear end 52 of which is bolted to the rear end of a heel spring 48, and the forward end 54 of which is bolted to the toe spring 42 intermediate its ends.

It will be appreciated that the foot 40 would also be secured within a cosmesis (not shown).

Thus, the toe and heel springs 42 and 48 are independently secured to the rigid carrier 46, but away from these connection regions they are secured to one another by the wave spring 50. The provision of a further spring member for the foot thus allows a further opportunity for adjustment of the responses of the foot to be tuned to the specific requirements of the wearer. Furthermore, a wave spring may be arranged to act as a strain limiter to protect one or both of the resilient foot members from overload. The load required to straighten the wave spring, and the resulting energy stored therein, complements the toe and heel members. However, should the wave spring become straightened, then it will become substantially rigid. Thus, with the wave spring fully extended, the heel member directly supports the toe member, and vice versa.

The toe portion of the foot may be split longitudinally to accommodate M-L movement.

It will be appreciated that individual features of the various embodiments disclosed herein maybe combined with individual features of other embodiments as required.

What is claimed is:

1. A prosthetic foot comprising:
    a substantially two-dimensional, resilient toe member;
    a substantially two-dimensional, resilient heel member; and
    a substantially rigid carrier member; wherein one end of each of the toe and heel members is connected to the carrier member and each of said toe and heel members operate independently of the other of said members, and wherein the toe member extends forwardly and substantially unidirectionally from its connection with the carrier member and the heel member extends rearwardly and substantially unidirectionally from its connection with the carrier member.

2. A prosthetic foot according to claim 1, wherein the toe and heel members overlap one another in the region between the connections.

3. A prosthetic foot according to claim 1 wherein the toe member extends over the heel member.

4. A prosthetic foot according to claim 1, wherein the carrier member defines an enclosure, and wherein one end of each of the toe and heel members extends into the enclosure and is secured therewithin, and wherein the other end of each of the toe and heel members is secured to the outside of the enclosure.

5. A prosthetic foot according to claim 1, wherein at least one of the toe and heel members is concave, preferably channel-shaped, over at least part of its length.

6. A prosthetic foot according to claim 1, wherein the carrier is provided with a stop, to limit resilient movement of at least one of the toe and heel members.

7. A prosthetic foot according to claim 1, wherein the carrier member comprises an attachment for a prosthetic ankle joint.

8. A prosthetic foot according to claim 1, wherein the toe and/or heel member is made from a high strength, resin-impregnated fibrous material.

9. A prosthetic foot according to claim 8, wherein the material comprises carbon fibre.

10. A prosthetic foot according to claim 1, wherein the carrier member is made from a lightweight composite, high strength material.

11. A prosthetic foot according to claim 1, wherein the toe member is split longitudinally along at least part of its length, thereby to facilitate lateral movement of the foot in use.

12. A prosthetic foot according to claim 1, comprising a cosmesis, and wherein the other end of each of the toe and heel members is secured within the cosmesis.

13. A prosthetic foot according to claim 1, wherein the carrier member comprises a rectilinear cage.

14. A prosthetic foot according to claim 1, wherein said carrier member is elongated and extends longitudinally of said toe and heel members and comprises a forward portion and a rearward portion, wherein an end of said toe member is connected to the rearward portion of said carrier member, and an end of said heel member is connected to the forward portion of said carrier member.

15. A prosthetic foot comprising:

a substantially two-dimensional, resilient toe member;

a substantially two-dimensional, resilient heel member; and a substantially rigid carrier member; wherein one end of each of the toe and heel members is connected to the carrier member and each of said toe and heel members operate independently of the other of said members, and wherein the toe member extends forwardly and substantially unidirectionally from its connection with the carrier member and the heel member extends rearwardly and substantially unidirectionally from its connection with the carrier member; and a substantially resilient member secured to each of said toe and heel members at locations spaced apart from the respective connections of said toe and heel members to said carrier member.

16. A prosthetic fool comprising:

a substantially two-dimensional, resilient toe member;

a substantially two-dimensional, resilient heel member; and a substantially rigid carrier member that is elongated and extends longitudinally of said toe and heel members, wherein an end of each of said resilient toe and heel members is connected to said carrier member, and each of said toe and heel members operate independently of the other of said members, and wherein said toe member is substantially horizontally disposed and extends forwardly and substantially unidirectionally from its connection with said carrier member, and said heel member is substantially horizontally disposed and extends rearwardly and substantially unidirectionally from its connection with said carrier member.

* * * * *